United States Patent [19]

Pinto

[11] 4,367,206

[45] Jan. 4, 1983

[54] METHOD FOR PRODUCING METHANOL AND AMMONIA

[75] Inventor: Alwyn Pinto, Stockton-on-Tees, England

[73] Assignee: Imperial Chemical Industries Limited, London, England

[21] Appl. No.: 324,377

[22] Filed: Nov. 23, 1981

Related U.S. Application Data

[63] Continuation of Ser. No. 90,916, Nov. 5, 1979, abandoned.

[30] Foreign Application Priority Data

Nov. 10, 1978 [GB] United Kingdom ............... 43955/78

[51] Int. Cl.³ .............................................. C01C 1/04
[52] U.S. Cl. .................................... 423/359; 518/702; 518/704; 518/706; 518/708
[58] Field of Search ............... 518/702, 706, 708, 704; 423/359, 360, 361

[56] References Cited

U.S. PATENT DOCUMENTS

| | | | |
|---|---|---|---|
| 368,123 | 8/1887 | Arnois | 423/437 |
| 2,118,829 | 5/1938 | Storch | 423/437 |
| 3,598,527 | 8/1971 | Quartulli et al. | 423/361 |
| 3,689,575 | 9/1972 | Tarhan | 260/449.5 |
| 3,940,428 | 2/1976 | Connell et al. | 260/449.5 |
| 4,054,644 | 10/1977 | Segura et al. | 423/437 |
| 4,126,581 | 11/1978 | Sugier et al. | 423/656 |
| 4,153,671 | 5/1979 | Clements et al. | 423/656 |

FOREIGN PATENT DOCUMENTS

| | | |
|---|---|---|
| 836984 | 3/1970 | Canada ............................... 423/363 |
| 1567710 | 7/1970 | Fed. Rep. of Germany . |
| 55-67501 | 5/1980 | Japan . |
| 137206 | 3/1930 | Switzerland . |
| 258887 | 1/1928 | United Kingdom . |
| 366268 | 2/1932 | United Kingdom . |
| 1159035 | 7/1969 | United Kingdom . |
| 1159826 | 7/1969 | United Kingdom . |
| 1502190 | 2/1978 | United Kingdom . |
| 314432 | 11/1980 | United Kingdom . |

OTHER PUBLICATIONS

Japanese Published Application 55067501.
Golembiewski, Erdol-Kohle-Erdgas-Petrochemie, 1976, 29(2), 61–63.
Butzert, Chemical Engineering Progress, Jan. 1976, 56–59.
Supp. Nitrogen No. 109, Sep./Oct. 1977, 36–40.
"Steam Hydrocarbon Reforming seen as Integrated Processing Hub", The Oil and Gas Journal, (Jan. 10, 1972), pp. 53–58.
Hokari, "Methammonia Process", Chemical Economy & Engineering Review (Nov. 1972), vol. 4, No. 11, (No. 55), pp. 32 and 33.

Primary Examiner—Earl C. Thomas
Assistant Examiner—Wayne A. Langel
Attorney, Agent, or Firm—Cushman, Darby & Cushman

[57] ABSTRACT

A process for producing methanol and ammonia by generating nitrogen-containing synthesis gas, reacting the carbon oxides and hydrogen incompletely to methanol and passing the unreacted gas to ammonia synthesis, is characterized by carrying out the methanol synthesis in a first, steam-free, stage and in a second stage in the presence of sufficient steam to convert to carbon dioxide substantially all the carbon monoxide not converted to methanol. Methanol can be taken from the systhesis stage as part of the product or can be recycled to that stage, thus limiting its methanol output.

8 Claims, 1 Drawing Figure

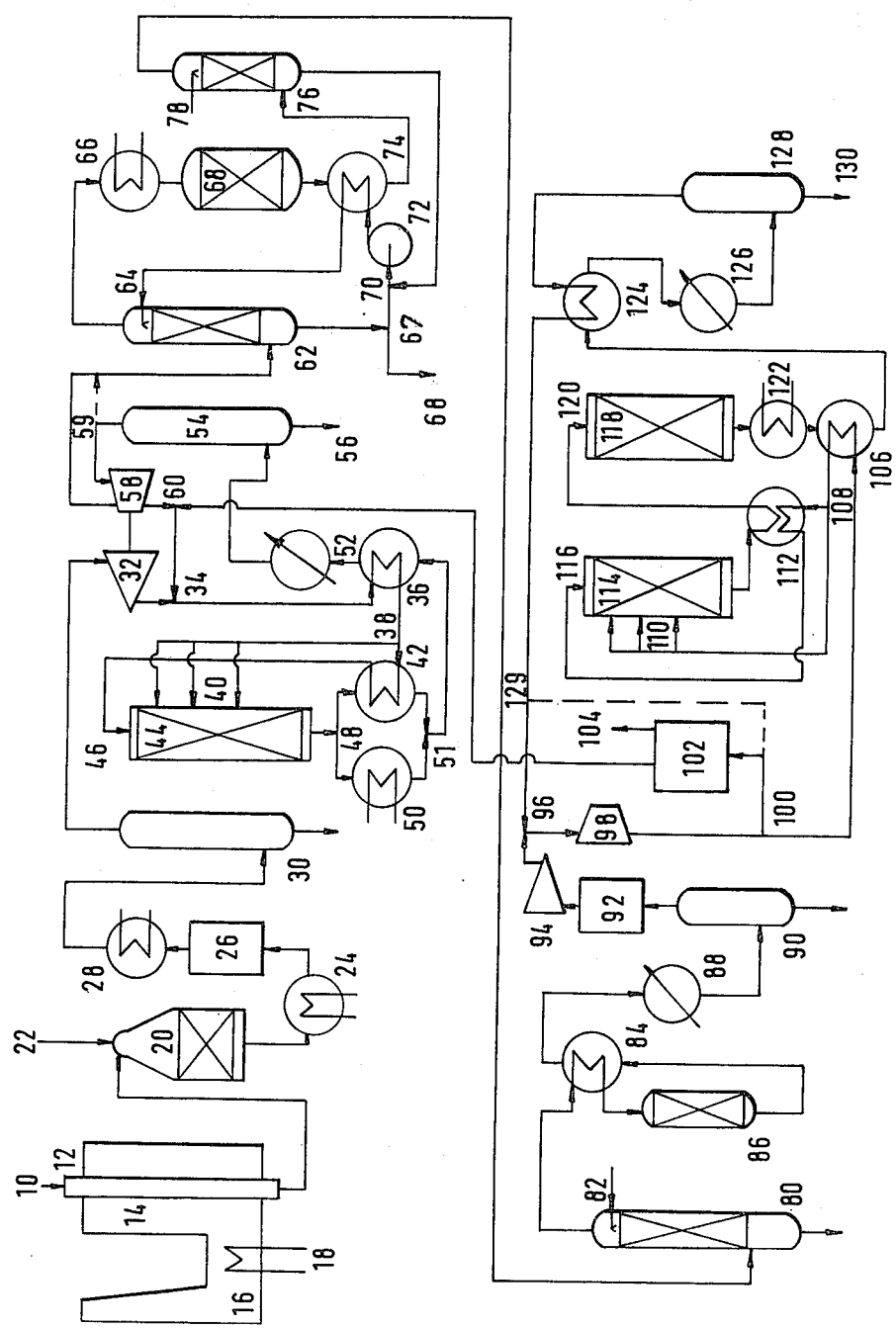

METHOD FOR PRODUCING METHANOL AND AMMONIA

This is a continuation of application Ser. No. 90,916 filed Nov. 5, 1979, now abandoned.

This invention relates to synthetic products and in particular to the production of methanol and ammonia in an integrated process.

Since ammonia synthesis gas has usually been made by reacting a carbonaceous feedstock with steam to give a raw gas containing carbon monoxide and hydrogen, it has been proposed to remove carbon monoxide by reacting it with part of the hydrogen in a methanol synthesis reaction, then to recover the methanol and react the remaining hydrogen with nitrogen to produce ammonia. Industrial use of a process of this kind has taken place, but substantially all the methanol plants and ammonia plants built since the mid 1960s have produced one product only. Proposals made in U.S. Pat. No. 3,598,527 and in Chemical Economy and Engineering Review 1972, 4 (11), 32-33 are subject to the defects inter alia respectively of complication and of inflexibility. A description of two integrated processes for producing methanol and ammonia is to be found in Quartulli, Oil and Gas Journal, Jan. 10, 1972, 53-58.

According to the invention a process for producing methanol and ammonia comprises the steps (a) generating a synthesis gas containing carbon oxides, nitrogen and hydrogen;

(b) reacting the synthesis gas over a copper-containing methanol synthesis catalyst whereby to convert the carbon oxides and hydrogen incompletely to methanol;

(c) separating the methanol and passing the unreacted gas to a catalytic ammonia synthesis;

and is characterised by carrying out step (b) in two stages, the first in the substantial absence of initially present water vapour and the second in the presence of sufficient water vapour to convert to carbon dioxide substantially all the carbon monoxide not converted to methanol.

After the second part of step (b) an aqueous methanol condensate is recovered and the carbon dioxide is removed by known means.

Step (a) can be any suitable gasification process, for example non-catalytic partial oxidation of coal, residual hydrocarbon or vaporisable hydrocarbon, catalytic partial oxidation of vaporisable hydrocarbon or catalytic steam reforming. Catalytic steam reforming is conveniently carried out in two stages:

(i) primary catalytically reforming a hydrocarbon feedstock with steam to give a gas containing carbon oxides, hydrogen and methane;

(ii) secondary catalytically reforming the gas from stage (i) by introducing air and bringing the mixture towards equilibrium, whereby to produce a gas containing nitrogen, carbon oxides, hydrogen and a decreased quantity of methane.

The hydrocarbon feedstock is preferably methane or other steam reformable hydrocarbon such as a normally gaseous or liquid hydrocarbon boiling at up to about 220° C. The primary catalytic reforming can itself be in one stage, over a catalyst with external heating or, when the feedstock is of a higher molecular weight than methane and especially when it is normally liquid, can be in two stages, in the first of which the feedstock is converted to a gas of high methane content at an outlet temperature under 650° C. and in the second of which that gas is reacted in the externally heated process. Various types of supported nickel catalyst are available for these hydrocarbon-steam reactions. The feedstock preferably should be substantially sulphur-free (under 0.5 ppm S) and may have been subjected to a preliminary catalytic hydrodesulphurisation and $H_2S$-removal treatment.

In a primary steam reforming process the pressure is suitably in the range 10–100, more conveniently 15–40 bar abs. The outlet temperature is suitably in the range 750°–950° C. and the molar steam to carbon ratio 2.0 to 3.5. The methane content of the primary reformer gas is typically 2–10% v/v on a dry basis.

The feed to secondary reforming includes the primary reformer gas, which may, if desired, be further heated, and an oxygen-containing gas, conveniently air or enriched air, which preferably is preheated to a temperature in the range 400°–700° C. Further steam or hydrocarbon can be fed. The secondary reformer outlet temperature is suitably in the range 900°–1050° C. and the outlet methane content in the range 0.2 to 1.0% on a dry basis. In order to provide for variation of the relative outputs of methanol and ammonia, there may be means to change the feed rate of the air and/or to change the oxygen to nitrogen ratio.

Provision may be made for heat exchange between secondary reformer outlet gas and a steam-hydrocarbon mixture undergoing primary reforming.

Heat is recovered from the gas produced in step (a) and from furnace flue gases if an externally heated process is used. The gas then is cooled with the recovery of useful heat to the temperature at which steam can be removed, either by indirect heat exchange with condensation and separation or else by contact with liquid water to produce a hot water stream. Especially if the initial synthesis gas generation uses a feedstock containing fewer than about 2.5 hydrogen atoms per carbon atom or is a partial oxidation, cooling is first to the inlet temperature of a shift reaction, for example in the range 300°–400° C., especially 320°–350° C. appropriate to iron-chrome shift catalysts. The reaction over the iron-chrome catalyst is exothermic (outlet temperature 400°–450° C.) and the outlet gas is again cooled with recovery of useful heat in a similar manner to the cooling of process gas from step (a). If the gas contains sulphur compounds an analogous shift system based on catalysts containing other Group VI and Group VIII metals and oxides or on alkali metal compounds of weak acids is used and analogous heat recoveries are effected. After a shift stage, cooling and steam removal, the gas is contacted with a regenerable carbon dioxide absorbent liquid, for example, potassium carbonate solution or an ethanolamine. If sulphur compounds are present they can be removed, for example, by means of a metal oxide, after removal of steam and/or carbon dioxide. As an alternative the steam can be removed and the gas subjected to a liquid, such as methanol, that absorbs carbon dioxide and also removes sulphur compounds thoroughly enough to make the metal oxide treatment unnecessary except as a guard to the methanol synthesis catalyst.

Shift and $CO_2$-removal steps can be introduced or designed to increase the rate of $CO_2$-removal when it is desired to increase the output of ammonia and decrease the output of methanol. Such a system is useful also when the initial synthesis gas generation uses a feedstock containing 2.5 or more hydrogen atoms per carbon atom. When there is a $CO_2$ removal step before methanol synthesis the absorbent solution used is conveniently from the same stock as in the step after methanol synthesis and a common solution regenerator is preferably used.

When there is no such $CO_2$-removal step the output of methanol can be decreased by passing a side stream of gas directly to the second methanol synthesis stage or, after $CO_2$ removal, to either methanol synthesis stage.

The methanol synthesis can be at any suitable pressure, for example in the range 30 to 120 bar abs. but is most conveniently in the range 40 to 100 bar abs. If the steps of shift and $CO_2$-removal and also of preceding partial oxidation and purification are at a pressure at least 90% of that of the synthesis, no compression or at most the degree of compression afforded by a synthesis gas circulator will be required. Using synthesis gas made by primary and secondary reforming a compressor is normally required and the pressure increase is suitably by a factor of 2 to 5.

Preferably the compressor used is separate from the synthesis gas circulator, if the methanol synthesis is a recycle process. Using a separater compressor it is more convenient to take the side stream of fresh synthesis gas and subject it to $CO_2$-removal in order to decrease the output of methanol relative to ammonia.

A variety of general types of methanol synthesis process can be used. Usually these differ in the methods adopted for handling the heat evolved in the synthesis reaction. Any one or more of these can be used, including those designed to use directly all the relatively low pressure ("intermediate pressure") steam generated by heat exchange with the reacting gas or reacted gas in the synthesis. Suitable processes are described in our U.K. Pat. Nos. 1,484,366 and 1,484,367. As described therein, the synthesis preferable is carried out in a quench-cooled reactor; the temperature of quench gas can be below 50° C., but thermal efficiency is better if it is at between 50° and 150° C. The volume space velocity of the flow of gas through the synthesis catalyst bed is typically in the range 5000–50000 hour$^{-1}$ and is adjusted to suit the output of methanol required. The catalyst outlet temperature is under 300° C. and preferably under 280° C. The methanol content of the reacted gas from the preferred quench cooled synthesis is for example 2–5% for a process at 50 bar abs. and proportionately more at higher pressures. Unreacted carbon oxides and hydrogen left over after methanol has been recovered are in part passed again over a methanol synthesis catalyst, for example, by recirculation to the inlet of the catalyst and mixing with fresh synthesis gas and in part "purged" to provide the gas to be used for ammonia synthesis.

The methanol synthesis catalyst usually contains also zinc and one or more further oxides, such as of chromium (our U.K. Pat. No. 1,010,871) or metals from Groups III–IV of the Periodic Table, especially aluminium (our U.K. Pat. No. 1,159,035) or possibly manganese or vanadium.

The product of the first stage of methanol synthesis typically contains 8–30% w/w of water and can be purified by distillation, for example as described in our U.K. Pat. No. 1,373,159 or application No. 10403-32399/77 which has been published as German application No. P 2808025.

In the first methanol synthesis stage the output is adjustable by known means, for example by changing the pressure, gas circulation rate or inlet temperature, to suit the relative outputs of methanol and ammonia required. In a convenient form of the process this stage is operated to give an unreacted gas containing between 2 and 6% v/v of carbon monoxide. The second stage can then be operated in a simple adiabatic reactor.

The unreacted gas from the first stage is at a pressure typically in the range 35 to 95 bar abs. This means that a conventional low temperature shift (LTS) process for converting carbon dioxide is impracticable, on account of the substantial methanol formation. A copper-containing catalyst is preferably used and may be of the LTS type, since these are formulated to operate in the presence of steam. The steam to dry gas ratio of the gas entering this stage is suitably in the range 0.1 to 0.3 by volume. The second stage reaction temperature can be the same as in the first stage.

The reacted gas leaving the catalyst of the second methanol synthesis stage is cooled, possibly with heat recovery, and a condensate containing methanol (usually up to 20% w/w) and water is separated. Separation of such condensate is preferably in two stages, the first by mere cooling, the second by washing with water, so as to remove residual methanol vapour.

The condensate or either part of it can be treated to recover methanol from it, for example by passing it to the distillation plant purifying the product of the first synthesis stage. Typically the second stage then produces 5 to 25% of the total methanol output. Very suitably, however, such condensate is recycled as the source of the steam fed to the second synthesis stage. When, as is preferred, this is done by vaporising the methanol-water mixture and adding the vapour to the feed to the second synthesis stage, for example by direct heat exchange between such mixture and feed gas, this results in a methanol concentration at the catalyst inlet sufficient to limit or even suppress the net formation of methanol in this stage. Indeed, if the methanol content of the feed is by such recycling allowed to increase sufficiently, the outlet methanol content can be less than the inlet methanol content. This is not objectionable if the methanol output of the first synthesis stage is sufficient, because any decomposition of methanol in the second stage results in the formation of hydrogen, which will be used in the ammonia synthesis step.

It will be appreciated that the second stage of methanol synthesis could be regarded as a low temperature shift stage modified to take account of the problems caused by methanol synthesis. It is, however, believed that designation as a methanol synthesis stage, which may or may not be a methanol production stage, affords a better technical description.

In a preferred form of second methanol synthesis stage with such methanol recycle the methanol vapour contents of the gases at the inlet and outlet of the catalyst are at least 0.1% v/v calculated on the gases including steam, and more typically at least 1% and up to 6% v/v. The inlet and outlet methanol contents differ typically by up to 2% v/v positively or negatively.

The gas leaving the separation after the second methanol synthesis stage, which contains typically 0.05 to 0.5% carbon monoxide, is subjected to $CO_2$-removal. Unlike the $CO_2$-removal stage (if any) prior to methanol synthesis, this stage is required to remove $CO_2$ as completely as practicable. Consequently a 2-stage absorber is used. The solution containing a small proportion of $CO_2$ from the downstream absorption stage can be used in the absorber of a $CO_2$-removal stage prior to methanol synthesis. If the pressure is high enough, a physical solvent system can be used, for example "Sulfinol" (tetramethylene sulfone), "Selexol" (dimethyl ether of polyethyleneglycol), "Rectisol" (methanol), "Purisol" (N-methyl-2-pyrrolidone) or propylene carbonate. For this purpose the shifted gas can be compressed after the second methanol synthesis stage. (The above proper names are believed to be Registered Trade Marks in the major industrial countries).

Final carbon oxides removal is most conveniently carried out by catalytic methanation, suitably over a supported nickel catalyst at an outlet temperature in the range 250°–400° C. The resulting gas is then dried and compressed, suitably up to 150 bar abs., but is suitable for use in the synthesis with less than 50% compression and possibly no more than the increase in pressure (for example up to 20%) encountered in a synthesis gas circulator. Most suitably the ammonia synthesis pressure is in the range 50 to 120 bar abs. The "fresh" synthesis gas is preferably mixed with synthesis gas recycled from an ammonia removal stage. At the preferred synthesis pressures the attainable pass conversion over the synthesis catalyst is relatively low, giving an ammonia outlet concentration in the range 8 to 18% v/v. The ratio of recycled gas to fresh gas is suitable in the range 4 to 6.

The catalyst used in the ammonia synthesis can be of the usual composition, namely iron with promoting quantities of non-reducible oxides such as those of potassium, calcium, aluminium and others such as of beryllium, cerium or silicon. In order to afford maximum activity and thus to compensate for the lower rate of reaction due to low pressure, the iron catalyst may contain also cobalt, suitably to the extent of 1–20% w/w calculated as $Co_3O_4$ on the total oxidic composition from which the catalyst is made by reduction and in which the iron oxide is assumed to be all $Fe_3O_4$. The outlet temperature of the synthesis catalyst is preferably in the range up to 500° C., especially 350°–450° C. This is lower than has been usual, in order to obtain a more favourable synthesis equilibrium. The catalyst volume is suitably in the range 100–200 m$^3$ per 1000 metric tons per day output; suitably it is used in a cooled bed followed by an adiabatic bed.

After passing over the synthesis catalyst the synthesis gas is cooled, suitably with one or more of the known heat recoveries, and ammonia is separated from it. Preferably cooling is finally to $-3°$ to $-10°$ C., to give anhydrous liquid ammonia, and the gas recycled contains 3 to 6% v/v of ammonia. Part of the unreacted gas is purged, treated to recover ammonia from it and then preferably treated, for example, cryogenically or by adsorption, to separate a hydrogen rich stream and a discard stream containing noble gases, methane and any excess nitrogen. The hydrogen-rich stream is recycled preferably to the inlet of the first methanol synthesis stage.

The drawing is a flowsheet of one preferred form of the invention.

The starting materials steam and desulphurised hydrocarbon such as natural gas are preheated and fed at 10 into tubes 12 which contain a supported nickel catalyst and are heated in the radiant section 14 of the steam reforming furnace. Combustion gases from radiant section 14 pass to stack via convective section 16 in which heat is recovered from them by one or more of reactants preheating, steam superheating, steam generation, boiler feed water heating, process air heating and furnace combustion air heating in heat exchangers indicated generally by 18. The hot primary reformer gas (CO, $CO_2$, $H_2$, $CH_4$ and excess steam) leaves tube 12 and enters secondary reformer 20 in the upper region of which it reacts exothermally, with hot air fed in at 22 from a compressor (not shown) operated without final-stage cooling. The heat evolved in the exothermic reaction is absorbed by endothermic methane-steam reaction over the secondary reformer catalyst, which is suitably supported nickel or supported chromia or a combination thereof. The resulting gas is cooled at 24 with high grade heat recovery by one or more of reactants preheating, steam superheating or steam generation to high temperature shift (HTS) inlet temperature and then in low grade heat recoveries at 28 until its temperature is below the dewpoint of steam. If the HTS stage 26 is used, the heat exchanges represented by 28 include a further high grade heat recovery before the low grade heat recoveries. Water is separated at 30 and may be discarded or, after treatment, used as boiler feed water. Separator 30 could, if desired, be replaced by a dehumidifier fed with cold water.

The relatively dry gas passing overhead from separator 30 is compressed at 32 to methanol synthesis pressure and united at 34 with a mixture of unreacted methanol synthesis gas and a hydrogen stream recovered from the ammonia synthesis section, which gas and stream will be further described below. (If desired a side stream from 32 can be treated to remove $CO_2$ and a $CO_2$-depleted stream returned to the synthesis). The mixed gas is warmed in heat exchanger 36 and divided at 38 into (a) a quench stream to be fed to hollow bar distributors 40 in methanol synthesis catalyst bed 44 and (b) a main stream to be heated in heat exchanger 42 to the inlet temperature (suitably 240° C.) of catalyst bed 44, which it enters at 46. There may, if desired, be two or more such methanol synthesis reactors operated in parallel, in which event the warm gas pipe leaving point 38 and the hot gas pipe leaving heat exchanger 42 will each be furcate. The hot reacted methanol synthesis gas leaving the reactor or reactors is divided at point 48 into a preheat stream which is cooled in heat exchanger 42 already mentioned and a heat recovery stream which is cooled in pressurised boiler feed water heater 50. The cooled streams are re-united at point 51, cooled further in gas-warmer 36 and then cooled to below the dew-point of methanol in cooler 52. Aqueous methanol is separated in catchpot 54 and run off at 56 to a pressure let down vessel and distillation section (both not shown). Unreacted gas passes out to circulator 58, from which two streams are taken, namely (a) a recycle stream, which is united with $H_2$ at 60 and then fresh gas at 34; and (b) an ammonia synthesis stream. As an alternative, stream (b) can be taken at point 59 upstream of circulator 58 and passed out via the dotted path.

The ammonia synthesis stream, consisting of CO, $CO_2$, $H_2$, $N_2$, noble gases, a few percent of $CH_4$ and a fractional percentage of methanol vapour but very little water vapour is humidified in packed tower 62 down which flows hot water fed in at 64 and containing dissolved methanol. The resulting wet gas is heated at 66 to wet synthesis inlet temperature (suitably 210° C.), enters catalyst 68 and leaves at a higher temperature (suitably 247° C.) as a result of the exothermic shift reaction and methanol synthesis reaction. The hot gas is cooled in methanol/water heater 74 and freed of its content of steam and methanol vapour in scrubber 76, which is fed with cold water at 78. The hot methanol/water produced in heater 74 is used as the feed 64 to tower 62. The cooled methanol/water leaving the bottom of tower 62 is divided at point 67 into (a) purge stream 68 which is led off to methanol recovery in the distillation system to which stream 56 is fed; and (b) a return stream which is united at 70 with the weakly methanolic aqueous stream from scrubber 76 and fed via pump 72 to heater 74.

The scrubbed shifted gas is contacted in tower 80 with a $CO_2$-absorbing solution fed in at 82: for simplicity a single absorption stage is shown and the regeneration plant, to which the bottoms liquid from 80 is passed before being returned at 82, being conventional, has been omitted. The $CO_2$-freed gas is taken overhead, heated at 84 to methanation inlet temperature and passed over the methanation catalyst in reactor 86, in which substantially all its residual content of CO and $CO_2$ is converted to $CH_4$. The methanated gas is cooled in feed/effluent heat exchanger 84 and then cooled at 88 to below the dewpoint of steam, water being separated in catchpot 90.

The water-freed methanated gas is rigorously dried at 92 over a molecular sieve, compressed at 94 to ammonia synthesis pressure, united at 96 with a recycle gas stream to be described and fed through circulator 98 to point 100 at which the gas is divided into a major and a minor stream. The major stream is warmed in exchanger 106 and divided at 108 into a quench stream and a main feed stream. The quench stream is fed to inlets 110 in the quench cooled catalyst bed 114 of primary synthesis reactor 116. The main feed stream is heated in exchanger 112 to synthesis inlet temperature and fed to the inlet of bed 114. In bed 114 the gas reacts exothermally, whereafter it passes out, is cooled in exchanger 112 to synthesis inlet temperature and is fed to bed 118 of secondary synthesis reactor 120 which, owing to the nearness of the reaction mixture to equilibrium, does not include cooling means. The fully reacted gas is cooled at 122 in exchange with pressurised boiler feed water, cooled further in feed gas warmer 106 and recycle gas warmer 124, and chilled to the ammonia dewpoint in refrigerated heat exchanger 128. Liquid ammonia is separated in 128 and run off at 130. Unreacted gas is recycled via warmer 124 to the inlet of circulator 98.

Referring again to point 100, the minor stream passes into hydrogen recovery unit 102. As an alternative the hydrogen recovery stream is taken at point 129 upstream of circulator 98 and fed to unit 102 via the dotted path. In unit 102 this stream is separated into a discard stream 104 consisting mainly of methane, nitrogen and noble gases and a hydrogen-rich stream which is sent back to the inlet of the methanol synthesis section at point 60. The pressure at the outlet of unit 102 is high enough to drive the hydrogen-rich stream to point 60, even if the stream fed to unit 102 has been taken at point 129. (The hydrogen-rich stream could be recycled to the ammonia synthesis section, for example to the inlet of circulator 98, but we find that the process as shown is more easily controlled in its methanol-to-ammonia output ratio).

In a typical process according to the flowsheet producing methanol at 2500 and ammonia at 1065 metric tons per day, the pressures, temperatures and flow rates are as in the Table.

| Position | Temp °C. | Pressure bar abs. | Flow rate kg mol $h^{-1}$ | | | | | | |
|---|---|---|---|---|---|---|---|---|---|
| | | | CO | $CO_2$ | $H_2$ | $CH_4$ | $N_2$ | Ar | $CH_3OH$ |
| 38 | 108 | 80 | 2866 | 1087 | 11896 | 63 | 1553 | 19 | 20 |
| 48 | 270 | 72 | 300 | 285 | 4432 | 62 | 1545 | 19 | 325 |
| 68 out | 247 | 70 | 29 | 556 | 4703 | 62 | 1545 | 19 | 69 |
| 94 out | 30 | 90 | — | — | 4580 | 100 | 1545 | 19 | — |
| 102 - 60 | 30 | 90 | — | — | 561.5 | 52.5 | 220.5 | 19 | — |
| 104 | 30 | 90 | — | — | 9.0 | 47.5 | 21.5 | — | — |

This process is based on primary steam reforming of methane at a steam ratio 3.0, pressure 19.7 bar abs., primary outlet temperature 903° C., followed by secondary reforming with air at outlet temperature 1000° C. Using the two stage ammonia synthesis reactor the ammonia percentages v/v are typically 3.8 at first bed inlet, 11.9 at first bed outlet, 15.0 at second bed outlet and 4.9 at catchpot overhead. The weight ratio of methanol to ammonia produced is adjustable in the range 1.0 to 3.3.

I claim:

1. A process for producing methanol and ammonia comprising the steps of
   (a) generating a synthesis gas containing carbon oxides, nitrogen and hydrogen;
   (b) reacting the synthesis gas over a copper-containing methanol synthesis catalyst at a catalyst outlet temperature under 300° C. whereby to convert the carbon oxides and hydrogen incompletely to methanol;
   (c) separating the methanol and passing the unreacted gas to a catalytic ammonia synthesis;
   and characterised by carrying out step (b) in two stages, the first in the substantial absence of initially present water vapour and the second in the presence of sufficient water vapour to convert to carbon dioxide substantially all the carbon monoxide not converted to methanol in the said first stage, both of said first and second stages being operated at a catalyst outlet temperature under 300° C. and subjecting the unreacted methanol synthesis gas to no other shift stage, further characterised in that the first methanol synthesis stage is operated to produce an unreacted gas containing between 2% and 6% v/v of carbon monoxide, the pressure of the unreacted gas from the first methanol synthesis stage is in the range between 35 to 95 bar absolute, and the steam to dry gas ratio of the gas entering the second methanol synthesis stage is in the range between 0.1 to 0.3 by volume.

2. A process according to claim 1 in which condensate containing methanol and water separated after the second stage of methanol synthesis is recycled as the source of water vapor for that stage, whereby to limit its net output of methanol.

3. A process according to claim 2 in which the methanol vapour contents of the inlet and outlet gases of the second methanol synthesis stage catalyst are in the range 1 to 6% v/v calculated on the gases including steam and differ by up to 2% positively or negatively.

4. A process according to claim 1 in which condensate containing methanol and water separated after the second stage of methanol synthesis in step (b) is treated to recover methanol by passing it to the distillation plant purifying the product of the first synthesis stage in the said step (b).

5. A process according to claim 1 in which step (a) comprises
   (i) primary catalytically reforming a hydrocarbon feedstock with steam to give a gas containing carbon oxides, hydrogen and methane,
   (ii) secondary catalytically reforming the gas from stage (i) by introducing air and bringing the mixture towards equilibrium;
   and the feed rate of the air to stage (ii) or the oxygen to nitrogen ratio of that air are adjusted to suit the relative outputs of methanol and ammonia required.

6. A process according to claim 1 in which, in order to decrease the output of methanol relative to ammonia, a side stream of methanol synthesis gas is passed directly to the second stage of methanol synthesis.

7. A process according to claim 1 in which, in order to decrease the output of methanol relative to ammonia, a side stream of methanol synthesis gas is subjected to carbon dioxide removal and passed to either methanol synthesis stage.

8. A process according to claim 1 in which the feed to the first methanol synthesis stage includes a hydrogen rich stream produced by a separation treatment of a stream of unreacted gas purged from the ammonia synthesis after recovery of ammonia therefrom.

* * * * *